US010752633B2

(12) United States Patent
Anderson et al.

(10) Patent No.: US 10,752,633 B2
(45) Date of Patent: *Aug. 25, 2020

(54) HETEROAROMATIC NMDA RECEPTOR MODULATORS AND USES THEREOF

(71) Applicant: Cadent Therapeutics, Inc., Cambridge, MA (US)

(72) Inventors: David R. Anderson, Salem, CT (US); Robert A. Volkmann, Mystic, CT (US); Gregg F. Keaney, Lexington, MA (US); Steven C. Leiser, Valley Cottage, NY (US); Sam Malekiani, Watertown, MA (US); Timothy Piser, Wilmington, DE (US)

(73) Assignee: Cadent Therapeutics, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/678,806

(22) Filed: Nov. 8, 2019

(65) Prior Publication Data

US 2020/0131190 A1 Apr. 30, 2020

Related U.S. Application Data

(63) Continuation of application No. 16/530,274, filed on Aug. 2, 2019, now Pat. No. 10,584,131.

(60) Provisional application No. 62/714,100, filed on Aug. 3, 2018.

(51) Int. Cl.
C07D 487/04 (2006.01)
A61P 25/18 (2006.01)

(52) U.S. Cl.
CPC .................................. C07D 487/04 (2013.01)

(58) Field of Classification Search
CPC .............................. C07D 487/04; A61P 25/18
See application file for complete search history.

(56) References Cited

U.S. PATENT DOCUMENTS

| 4,921,854 | A  | 5/1990  | Bozsing et al.    |
|-----------|----|---------|-------------------|
| 6,852,731 | B2 | 2/2005  | Larsen et al.     |
| 10,500,205| B2 | 12/2019 | Anderson et al.   |
| 2007/0093509 | A1 | 4/2007 | Washburn et al.  |
| 2008/0064678 | A1 | 3/2008 | Letourneau et al.|
| 2008/0090802 | A1 | 4/2008 | Letourneau et al.|
| 2008/0214553 | A1 | 9/2008 | Letourneau et al.|
| 2008/0280900 | A1 | 11/2008| Pajouhesh et al. |
| 2010/0249087 | A1 | 9/2010 | Wang et al.      |
| 2012/0165330 | A1 | 6/2012 | Vu               |
| 2012/0178742 | A1 | 7/2012 | Henrich et al.   |
| 2013/0123231 | A1 | 5/2013 | Harriman et al.  |
| 2016/0222033 | A1 | 8/2016 | Yu et al.        |
| 2017/0305861 | A1 | 10/2017| Kim et al.       |
| 2017/0313719 | A1 | 11/2017| Traynelis et al. |
| 2018/0360837 | A1 | 12/2018| Anderson et al.  |
| 2018/0362541 | A1 | 12/2018| Anderson et al.  |

FOREIGN PATENT DOCUMENTS

| CN | 102336768 A   | 2/2012  |
|----|---------------|---------|
| WO | 1998/00401 A1 | 1/1998  |
| WO | 2008/076883 A2| 6/2008  |
| WO | 2008/097538 A1| 8/2008  |
| WO | 2008/128982 A1| 10/2008 |
| WO | 2009/025784 A1| 2/2009  |
| WO | 2009/062930 A1| 5/2009  |
| WO | 2009/134973 A1| 11/2009 |
| WO | 2009/146358 A1| 12/2009 |
| WO | 2010/003048 A1| 1/2010  |
| WO | 2010/037127 A1| 4/2010  |
| WO | 2010/037129 A1| 4/2010  |
| WO | 2010/079443 A1| 7/2010  |
| WO | 2010/111573 A1| 9/2010  |
| WO | 2010/139483 A1| 12/2010 |
| WO | 2011/045258 A1| 4/2011  |
| WO | 2011/117381 A1| 9/2011  |
| WO | 2011/117382 A1| 9/2011  |
| WO | 2012/052540 A1| 4/2012  |
| WO | 2012/129562 A2| 9/2012  |
| WO | 2013/048928 A1| 4/2013  |
| WO | 2013/048942 A1| 4/2013  |
| WO | 2013/049104 A2| 4/2013  |
| WO | 2014/139325 A1| 9/2014  |
| WO | 2014/179144 A1| 11/2014 |
| WO | 2014/206343 A1| 12/2014 |
| WO | 2015/007453 A1| 1/2015  |
| WO | 2015/096611 A1| 7/2015  |
| WO | 2016/034703 A1| 3/2016  |
| WO | 2016/081649 A1| 5/2016  |
| WO | 2017/066590 A1| 4/2017  |

(Continued)

OTHER PUBLICATIONS

Almasi et al., Characterization of potential NMDA and cholecystokinin antagonists. II. Lipophilicity studies on 2methyl-4-oxo-3H-quinazoline-3-alkyl-carboxylic acid derivatives. International Journal of Pharmaceuticals. Mar. 1, 1999;180(1)13-22.

Jia et al., Identification, design and bio-evaluation of novel Hsp90 inhibitors by ligand-based virtual screening. PLoS One. 2013;8(4):e59315, 15 pages.

Napier et al., Synthesis and SAR studies of novel 2-(6-aminomethylaryl-2-aryl-4-oxo-quinazolin-3(4H)-yl)acetamide vasopressin V1b receptor antagonists. Bioorg Med Chem Lett. Jun. 15, 2011;21(12):3813-7.

Nerkar et al., In Silico Design, Synthesis and Pharmacological Screening of Novel Mono and Di-Bromo Quinazolinone Derivatives as NMDA Receptor Antagonists for Anticonvulsant Activity. International Journal of Pharmacy and Pharmaceutical Sciences. 2013;5(1)331-335.

(Continued)

Primary Examiner — Sahar Javanmard
(74) Attorney, Agent, or Firm — McCarter & English, LLP; Steven G. Davis; Michael J. DeGrazia

(57) ABSTRACT

Provided is 5-(3-chloro-4-fluorophenyl)-7-cyclopropyl-3-(2-(3-fluoro-3-methylazetidin-1-yl)-2-oxoethyl)-3,7-dihydro-4H-pyrrolo[2,3-d]pyrimidin-4-one and pharmaceutically acceptable salts thereof, and their uses in the treatment of psychiatric, neurological, and neurodevelopmental disorders, as well as diseases of the nervous system.

5 Claims, 2 Drawing Sheets

(56) References Cited

FOREIGN PATENT DOCUMENTS

| WO | 2017/100591 A1 | 6/2017 |
| WO | 2017/100593 A1 | 6/2017 |
| WO | 2017/100599 A1 | 6/2017 |
| WO | 2017/188694 A1 | 11/2017 |
| WO | 2018/026371 A1 | 2/2018 |
| WO | 2018/119374 A1 | 6/2018 |

OTHER PUBLICATIONS

Noueiry et al., Identification of Novel Small-Molecule Inhibitors of West Nile Virus Infection. J Virol. Nov. 2007; 81 (21):11992-12004.
PUBCHEM-CID 10587973, Create Date: Oct. 25, 2006, 9 pages.
PUBCHEM-CID 16957685, 8-(4-tert-butylphenyl)-6-oxo-3,4-dihydro-2H,6H-pyrimido[2,1-b][1,3]thiazine-7-carbonitrile. Create Date: Nov. 13, 2007, 7 pages.
PUBCHEM-CID 6612590, 7-phenyl-8H-[1,2,4]triazolo[4,3-a] pyrimidin-5-one. Create Date: Jun. 5, 2006, 8 pages.
Santangelo et al., Novel NMDA receptor modulators: an update. Expert Opin Ther Pal Nov. 2012;22(11):1337-52.
STN Registry No. 924249-59-2, Thieno[2,3-d]pyrimidin-4(3H)-one, 3-[3-(1-azetidinyl)-3-oxopropyl]-5-(4-methylphenyl)-, dated Mar. 2, 2007, 3 pages.

*P<0.05 vs Vehicle, **P,0.05 vs MK-801, 1-way ANOVA, Dunnet's Post-Hoc

HETEROAROMATIC NMDA RECEPTOR MODULATORS AND USES THEREOF

RELATED APPLICATIONS

This application is a continuation of U.S. application Ser. No. 16/530,274 filed Aug. 2, 2019, which claims the benefit of priority to U.S. Provisional Application No. 62/714,100 filed Aug. 3, 2018, the entire contents of each of which are incorporated herein by reference.

BACKGROUND

Diseases of the nervous system are collectively the leading cause of human disability, as measured by the global burden of disease. Even those major diseases of the nervous system for which treatments have been approved by health authorities, including psychiatric diseases such as Schizophrenia, neurological diseases such as Alzheimer's Disease, and neurodevelopmental disorders, such as Attention Deficit and Hyperactivity Disorder, are poorly managed because approved treatments have limited efficacy and serious side effects, leaving a significant burden of unmet medical need. In addition, there are many major and rare nervous system disorders for which no treatments are approved, such as the neurodevelopmental disorders of the Autism Spectrum, and many intellectual disability disorders, and which are therefore associated with profound unmet medical need.

The N-methyl-D-aspartate-(NMDA) subtype of ligand-gated ion channel receptors are a diverse family of glutamate receptors widely accepted to mediate synaptic transmission, key mechanisms of synaptic plasticity, and dynamic neuronal network connectivity required for normal nervous system development and function.

The NMDA receptor is composed of four protein subunits, two GluN1 subunits and two GluN2 subunits. The GluN1 subunit is derived from a single gene (GRIN1), is ubiquitously expressed throughout the nervous system, and is common to all NMDA receptors. Four different GluN2 subunits, GluN2A-D, are derived from separate genes (GRIN2A-D) that are differentially expressed in different regions of the nervous system and by distinct populations of neurons within a particular region. A GluN3 subunit has also been identified, but its function is less well understood. Furthermore, individual neurons may express more than one GluN2 subunit and individual NMDA receptors expressed by such neurons may contain two of the same GluN2 subunits (for example, 2GluN2B subunits) or two different subunits (one GluN2A and one GluN2B subunit). In addition, all NMDA receptor subunits are expressed as diverse mRNA splice variants. Thus, native nervous system NMDA receptors are highly diverse in their composition.

The study of the molecular basis of NMDA receptor function continues to be an area of importance. As glutamate is the major excitatory neurotransmitter, dysfunction of glutamate neurotransmission and NMDA receptor-dependent mechanisms of synaptic transmission, plasticity, and neuronal network connectivity are broadly implicated in diseases of the nervous system. Accordingly, compounds that are capable of modulating NMDA receptors may be useful for the treatment of nervous system disorders and diseases, for example, schizophrenia, Alzheimer's disease, attention deficit and hyperactivity disorder, and autism.

SUMMARY

Provided herein is Compound 1, 5-(3-chloro-4-fluorophenyl)-7-cyclopropyl-3-(2-(3-fluoro-3-methylazetidin-1-yl)-2-oxoethyl)-3,7-dihydro-4H-pyrrolo[2,3-d]pyrimidin-4-one, having the following structure:

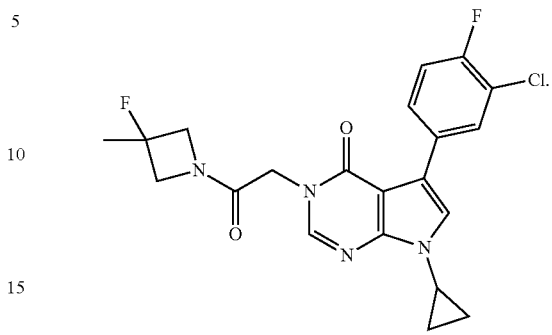

Compound 1 is a heterocyclic pyrrolopyrimidinone analogue which modulates NMDA receptors (e.g., positive allosteric modulation of NMDA receptors) and may be used for treating psychiatric, neurological, and neurodevelopmental disorders, as well as diseases of the nervous system.

Heterocyclic NMDA receptor modulators have been previously described in e.g., WO 2017/100591. In WO 2017/100591, a wide range of heterocyclic cores including pyrrolopyrazinones, thienopyridinones, imidazopyrazinones, pyrrolopyridinones, and pyrrolopyrimidinones are disclosed. The potency of the compounds in WO 2017/100591 was evaluated on the basis of the compounds' ability to reverse the suppression of the $Ca^{2+}$ response mediated by Ro 25-6981, a potent and selective antagonist of NMDA glutamate receptors containing the NR2B subunit, and 5,7-dichlorokynurenic acid (DCKA), a selective NMDA receptor antagonist acting at the glycine site of the NMDA receptor complex. Potency in the Ro 25-6981/DCKA assay was quantified by % response recovered (as shown e.g., in Table 49 of WO 2017/100591) and/or by % maximum measured potentiation. Of the most potent twenty-one analogs exemplified in WO 2017/100591 in the Ro 25-6981/DCKA assay and ranked by % response recovered, none were shown to be pyrrolopyrimidinone analogues.

There are forty-eight pyrrolo[2,3-d]pyrimidin-4-ones exemplified in WO 2017/100591. This pyrrolo[2,3-d]pyrimidin-4-one core is identical to the heterocyclic core of Compound 1. The most potent exemplified pyrrolo[2,3-d]pyrimidin-4-one based on % response recovered in the Ro 25-6981/DCKA assay exemplified in WO 2017/100591 was Example 174 (91% response recovered). See e.g., Table 49 of WO 2017/100591. Yet, as shown in Table 1 below, Compound 1 is approximately three-fold more potent than Example 174 in the disclosed oocyte NR2B PAM potentiation assay. Another exemplified pyrrolo[2,3-d]pyrimidin-4-one in WO 2017/100591 is Example 181. This compound was determined to be the most potent exemplified pyrrolo[2,3-d]pyrimidin-4-one based on the maximum measured potentiation (%) in the Ro 25-6981/DCKA assay. See Table 1 below for a comparison of Examples 174 and 181 in these two potency readouts from this Ro 25-6981/DCKA assay. Similar to the results with Example 174, Compound 1 was again found to be more potent (approximately 2.5-fold) in the disclosed oocyte NR2B PAM potentiation assay. Taking together, these results evidence the clinical potency advantage of Compound 1 over other pyrrolo[2,3-d]pyrimidin-4-one based scaffolds.

In terms of structurally related analogues, WO 2017/100591 discloses a constitutional isomer of Compound 1

(i.e., Example 436) as well as a one nitrogen variant (i.e., Example 285). Despite these structural similarities, Compound 1 was found to possess superior aqueous solubility, microsomal stability, and/or pharmacokinetic properties as compared to these two compounds. Table 2, for example, shows that Compound 1 has approximately a 10-fold increase in aqueous solubility over Example 436, the constitutional isomer of Compound 1. Compound 1 was found to have excellent cell permeability ($32 \times 10^{-6}$ cm/s for A→B and B→A) and was not a substrate for efflux in MDR1-transfected MDCK cells (efflux ratio=0.99). See Table 3. Table 4 shows that Compound 1 demonstrates significantly improved rat liver microsomal stability versus Example 285 ($t_{1/2}$>120 min versus 37.8 min, respectively) and also demonstrates significantly improved in vivo clearance in rat versus Example 285 (IV clearance=7.4 mL/min/kg versus 22.2 mL/min/kg) and several other analogs exemplified in WO 2017/100591.

The data above establishes numerous clinical advantages of Compound 1, thereby providing a solution to finding alternative NMDA modulators having e.g., improved potency, enhanced solubility, favorable microsomal stability and in vivo clearance, and excellent cell permeability.

DETAILED DESCRIPTION

1. Compounds

Figure 1:
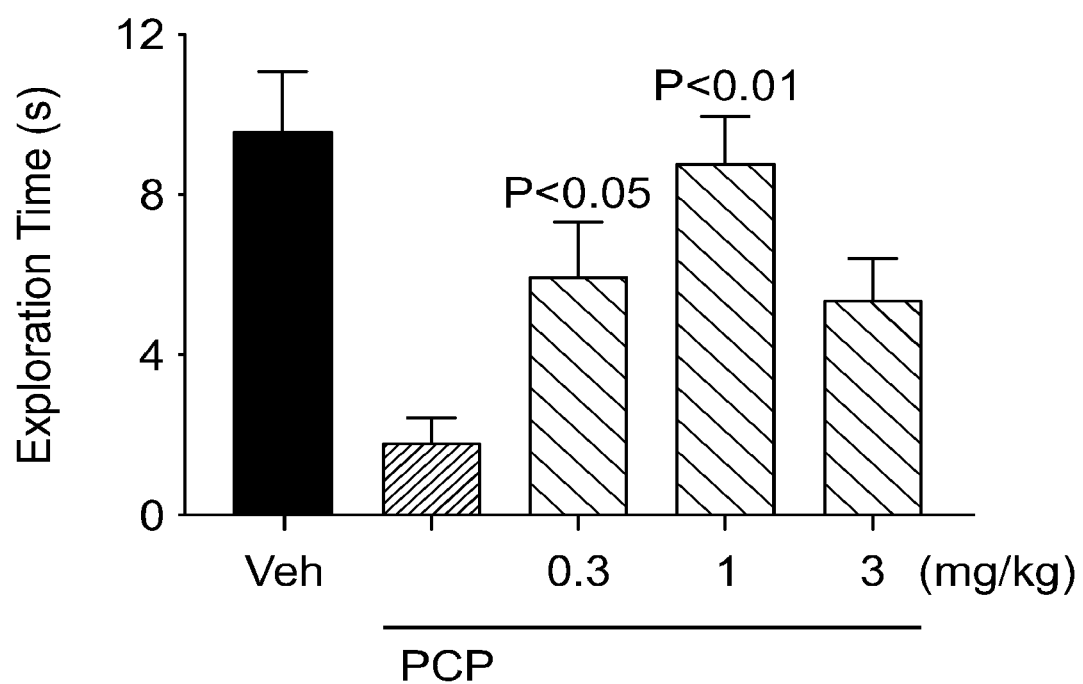
FIG. 1 illustrates the cognitive enhancing effect of oral Compound 1 (0.3, 1.0, and 3.0 mg/kg) against phencyclidine (PCP)-induced cognitive impairment in the rat Novel Object Recognition (NOR) test.

Provided herein is a compound having the following structure:

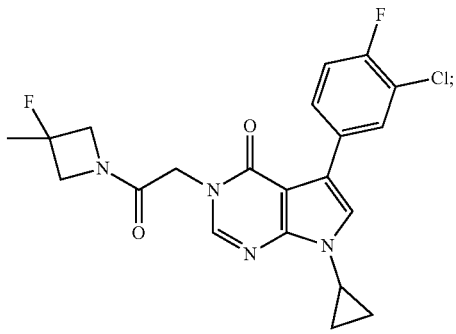 [SMILES: CC1(F)CN(C(=O)Cn2cnc3c(c(-c4ccc(F)c(Cl)c4)cn3C3CC3)c2=O)C1]

or a pharmaceutically acceptable salt thereof.

2. Definitions

As used herein the terms "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

Pharmaceutically acceptable salts as well as the neutral forms of the compounds described herein are included. For use in medicines, the salts of the compounds refer to non-toxic "pharmaceutically acceptable salts." Pharmaceutically acceptable salt forms include pharmaceutically acceptable acidic/anionic or basic/cationic salts. Pharmaceutically acceptable basic/cationic salts include, the sodium, potassium, calcium, magnesium, diethanolamine, n-methyl-D-glucamine, L-lysine, L-arginine, ammonium, ethanolamine, piperazine and triethanolamine salts. Pharmaceutically acceptable acidic/anionic salts include, e.g., the acetate, benzenesulfonate, benzoate, bicarbonate, bitartrate, carbonate, citrate, dihydrochloride, gluconate, glutamate, glycollylarsanilate, hexylresorcinate, hydrobromide, hydrochloride, malate, maleate, malonate, mesylate, nitrate, salicylate, stearate, succinate, sulfate, tartrate, and tosylate.

The term "pharmaceutically acceptable carrier" refers to a non-toxic carrier, adjuvant, or vehicle that does not destroy the pharmacological activity of the compound with which it is formulated. Pharmaceutically acceptable carriers, adjuvants or vehicles that may be used in the compositions described herein include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

"Pharmaceutically acceptable" means molecular entities and compositions that do not produce an adverse, allergic or other untoward reaction when administered to an animal, or a human, as appropriate.

The terms "treatment," "treat," and "treating" refer to reversing, alleviating, reducing the likelihood of developing, or inhibiting the progress of a disease or disorder, or one or more symptoms thereof, as described herein. In some embodiments, treatment may be administered after one or more symptoms have developed, i.e., therapeutic treatment. In other embodiments, treatment may be administered in the absence of symptoms. For example, treatment may be administered to a susceptible individual prior to the onset of symptoms (e.g., in light of a history of symptoms and/or in light of genetic or other susceptibility factors), i.e., prophylactic treatment. Treatment may also be continued after symptoms have resolved, for example to prevent or delay their recurrence.

The term "effective amount" or "therapeutically effective amount" includes an amount of a compound described herein that will elicit a biological or medical response of a subject e.g., a dosage of between 0.01-100 mg/kg body weight/day.

"Compound 1" and "5-(3-chloro-4-fluorophenyl)-7-cyclopropyl-3-(2-(3-fluoro-3-methylazetidin-1-yl)-2-oxo-ethyl)-3,7-dihydro-4H-pyrrolo[2,3-d]pyrimidin-4-one" are used interchangeably and each refer to the compound having the following formula:

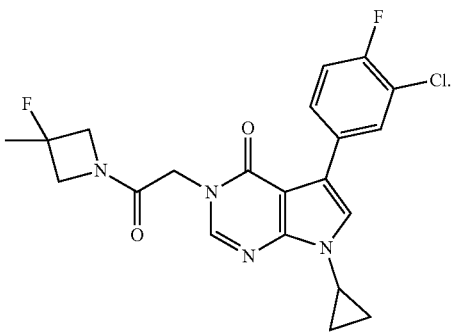 [SMILES: CC1(F)CN(C(=O)Cn2cnc3c(c(-c4ccc(F)c(Cl)c4)cn3C3CC3)c2=O)C1]

"PAM" refers to "positive allosteric modulator".

3. Uses, Formulation and Administration

In one aspect, Compound 1, or a pharmaceutically acceptable salt thereof and compositions described herein are useful in treating diseases and/or disorders associated with the activity of NMDA receptors. Such diseases and/or disorders include e.g., psychiatric, neurological, and neurodevelopmental disorders, as well as diseases of the nervous system.

In another aspect, Compound 1 or a pharmaceutically acceptable salt thereof and compositions described herein are useful for modulating the activity of the NMDA receptor.

In another aspect, Compound 1 or a pharmaceutically acceptable salt thereof and compositions described herein are useful for treating schizophrenia, Alzheimer's disease, attention deficit and hyperactivity, autism, and other nervous system-associated conditions.

In another aspect, Compound 1 or a pharmaceutically acceptable salt thereof and compositions described herein are useful for treating schizophrenia, including positive, negative, and cognitive symptoms. Schizophrenia is a debilitating mental disorder encompassing three symptom domains: positive (psychosis, hallucination, delusions), negative (withdrawal), and cognitive (global reduction in cognitive ability). Positive symptoms of schizophrenia typically emerge early in adulthood and are treated with antipsychotic medications. However, cognitive deficits are severe, emerge in the adolescent prodromal stage, are resistant to antipsychotic therapy, and are the leading cause of lifetime disability as measured by impaired global function (inability to live independently, unemployment, etc). NMDA receptor hypofunction is the leading hypothesis for the cause of schizophrenia. This hypothesis is supported by substantial clinical evidence including clinical pharmacology, electrophysiology, imaging, cognition, computational neuroscience, neuroanatomical studies, and genetics. In particular, several lines of evidence implicate hypofunction of NMDA receptors in schizophrenia. See Frank S. Menniti, Craig W. Lindsley, P. Jeffrey Conn, Jayvardhan Pandit, Panayiotis Zagouras, and Robert A. Volkmann, Allosteric Modulators for the Treatment of Schizophrenia: Targeting Glutamatergic Networks. Curr Top Med Chem. 2013; 13(1): 26-54.

In another aspect, Compound 1 or a pharmaceutically acceptable salt thereof and compositions described herein are useful for improving cognitive and global function, and/or preventing the onset of schizophrenia e.g., in people at risk of developing schizophrenia.

In another aspect, Compound 1 or a pharmaceutically acceptable salt thereof and compositions described herein are useful for treating cognitive and emotional deficits and other symptoms associated with exemplary psychiatric disorders including major depressive disorder, and including but not limited to those suffering from schizoaffective disorder, bipolar disorder, obsessive-compulsive disorder, dysphobic disorder, dysthymic disorder, psychotic depression, post-traumatic stress disorder, and other anxiety disorders. For example, provided herein are methods of treating attention deficit disorder, ADHD (attention deficit hyperactivity disorder), schizophrenia, anxiety, amelioration of opiate, nicotine and/or ethanol addiction (e.g., method of treating such addiction or ameliorating the side effects of withdrawing from such addiction), spinal cord injury, diabetic retinopathy, traumatic brain injury, and/or post-traumatic stress syndrome in a patient in need thereof, that includes administering Compound 1, or a pharmaceutically acceptable salt thereof, or a composition thereof.

In another aspect, Compound 1 or a pharmaceutically acceptable salt thereof and compositions described herein are useful for treating cognitive and emotional deficits and other symptoms resulting from neurological diseases, including but not limited to a patient suffering from mild cognitive impairment or any form of dementia, Alzheimer's disease, Parkinson's disease, Huntington's disease, amyotrophic lateral sclerosis, multiple sclerosis, and seizure disorders.

In another aspect, Compound 1 or a pharmaceutically acceptable salt thereof and compositions described herein are useful for treating dysfunction caused by neurodevelopmental disorders, e.g., abnormal brain development, including but not limited to Rett Syndrome, Attention Deficit and Hyperactivity Disorder, autism and autism spectrum disorders such as Phelan-McDermid Syndrome, and other forms of intellectual disability such as Fragile X syndrome, tuberous sclerosis, Smith-Lemli-Opitz Syndrome, Down syndrome and childhood epilepsies or epilepsy/aphasia spectrum disorders such as Benign partial Epilepsy of childhood with CentroTemporal Spikes (BECTS) or Landau-Kleffner Syndrome (LKS). A method is also provided to treat patients suffering from abnormal brain function resulting from infections of the central nervous system, exposure to toxic agents or other xenobiotics or naturally occurring toxins, and/or autoimmune disorders including, but not limited to anti-NMDA receptor encephalitis.

In another aspect, Compound 1 or a pharmaceutically acceptable salt thereof and compositions described herein are useful for treating subjects having NMDA receptor hypofunction.

Provided herein is a method of treating a subject having a disease, disorder, or condition described herein comprising administering to the subject a therapeutically effective amount of Compound 1, or a pharmaceutically acceptable salt thereof, or a composition thereof.

Also provided is the use of Compound 1, or a pharmaceutically acceptable salt thereof, or a composition thereof, for the manufacture of a medicament for treating a disease, disorder, or condition described herein.

Also provided is Compound 1, or a pharmaceutically acceptable salt thereof, or a composition thereof, for use in treating a disease, disorder, or condition described herein.

In one aspect, provided are pharmaceutically acceptable compositions comprising Compound 1; and a pharmaceutically acceptable carrier. These compositions can be used to treat one or more of the diseases, disorders, and conditions described above.

The disclosed compositions may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Liquid dosage forms, injectable preparations, solid dispersion forms, and dosage forms for topical or transdermal administration of a compound are included herein.

The amount of Compound 1 that may be combined with carrier materials to produce a composition in a single dosage form will vary depending upon the patient to be treated and the particular mode of administration. In some embodiments, provided compositions may be formulated so that a dosage of between 0.01-100 mg/kg body weight/day of the provided compound, such as e.g., 0.1-100 mg/kg body weight/day, can be administered to a patient receiving these compositions.

It should also be understood that a specific dosage and treatment regimen for any particular patient will depend upon a variety of factors, including age, body weight, general health, sex, diet, time of administration, rate of excretion, drug combination, the judgment of the treating physician, and the severity of the particular disease being treated. The amount of a provided compound in the composition will also depend upon the particular compound in the composition.

Combination therapies using a therapeutically effective amount of Compound 1, or a pharmaceutically acceptable salt thereof, and an effective amount of one or more additional pharmaceutically active agents is also included herein. In one aspect, for example, provided is the use of Compound 1, or a pharmaceutically acceptable salt thereof, and an effective amount of one or more atypical antipsychotics to treat a disorder or disease described herein. Atypical antipsychotics include, e.g., lurasidone, quetiapine, olanzapine, asenapine, risperidone, ziprasidone, clozapine, mel perone, cariprazine, aripiprazole, pimavanserin, ITI-007, RP506, and remoxipride.

EXEMPLIFICATION

The representative examples that follow are intended to help illustrate the present disclosure, and are not intended to, nor should they be construed to, limit the scope of the invention.

Example 1—Preparation of 5-(3-chloro-4-fluorophenyl)-7-cyclopropyl-3-(2-(3-fluoro-3-methylazetidin-1-yl)-2-oxoethyl)-3,7-dihydro-4H-pyrrolo[2,3-d]pyrimidin-4-one (Compound 1)

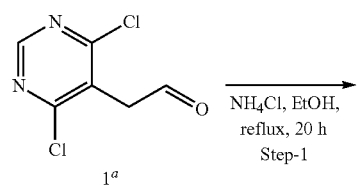

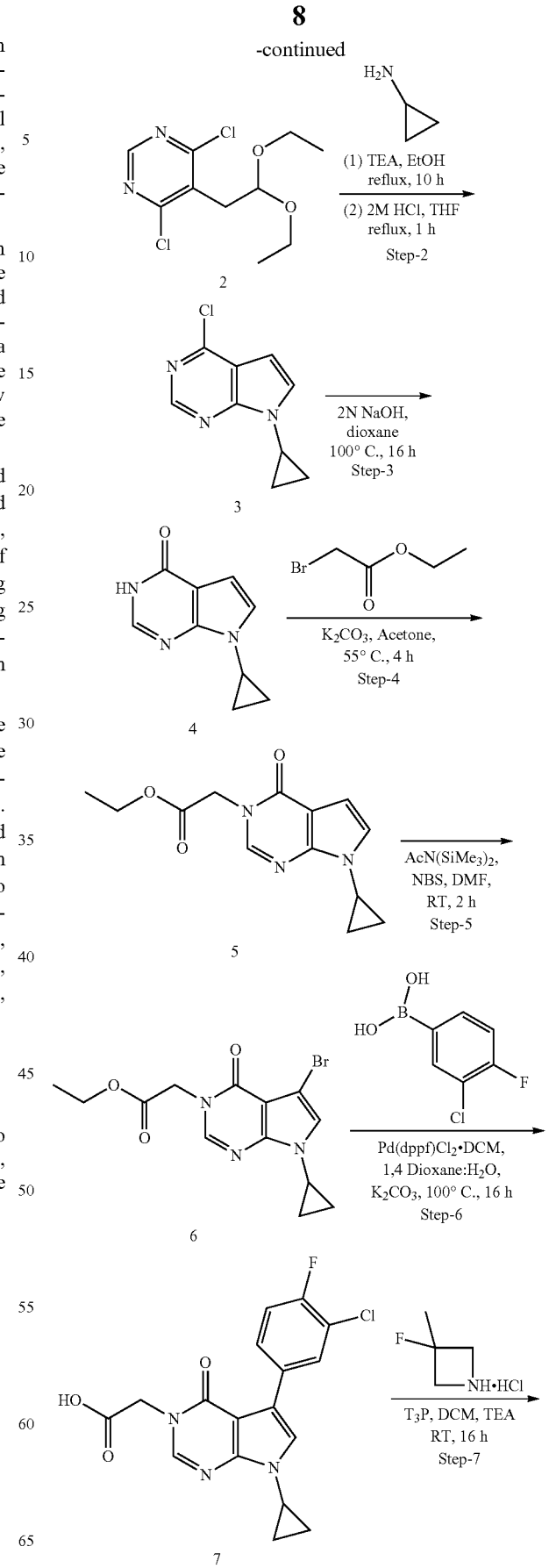

-continued

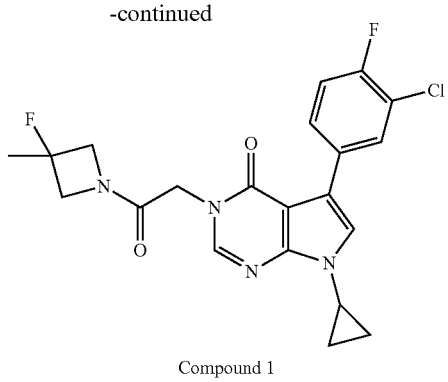

Compound 1

Step-1: Preparation of 4,6-dichloro-5-(2,2-diethoxyethyl)pyrimidine (2)

To a solution of 2-(4,6-dichloropyrimidin-5-yl)acetaldehyde (1, 5 g, 26.17 mmol) in ethanol (250 mL), ammonium chloride (2.11 g, 39.52 mmol) was added and the reaction mixture was refluxed for 20 h. The reaction mixture was concentrated; the residue was diluted with water (50 mL) and extracted with ethyl acetate (2×100 mL). The combined organic layer was dried over anhydrous sodium sulphate, filtered and concentrated to afford the title compound 4,6-dichloro-5-(2,2-diethoxyethyl)pyrimidine (2, 6.9 g, crude) as colorless oil. Calculated (M+H): 265.04; Found (M+H): 265

Step-2: Preparation of 4-chloro-7-cyclopropyl-7H-pyrrolo[2,3-d]pyrimidine (3)

To a solution of 4,6-dichloro-5-(2,2-diethoxyethyl)pyrimidine (2, 6.9 g, 26.02 mmol) and triethylamine (3.63 mL, 26.02 mmol) in ethanol (150 mL), cyclopropylamine (2 mL, 28.62 mmol) was added and the reaction mixture was refluxed for 10 h. The reaction mixture was evaporated under vacuum; the residue was diluted with water (100 mL) and extracted with ethyl acetate (2×200 mL). The combined organic layer was dried over anhydrous sodium sulphate, filtered and concentrated. The residue was dissolved in tetrahydrofuran (150 mL), 2M hydrochloric acid (75 mL) was added and the reaction mixture was refluxed for 1 h. The reaction mixture was concentrated, the residue was dissolved in water (100 mL), basified to pH 10 with sodium hydroxide solution and extracted with ethyl acetate (2×200 mL). The combined organic layer was dried over anhydrous sodium sulphate, filtered and concentrated to afford the title compound 4-chloro-7-cyclopropyl-7H-pyrrolo[2,3-d]pyrimidine (3, 5 g, crude) as brownish semi-solid. Calculated (M+H): 194.04; Found (M+H): 194

Step-3: Preparation of 7-cyclopropyl-3,7-dihydro-4H-pyrrolo[2,3-d]pyrimidin-4-one (4)

A solution of 4-chloro-7-cyclopropyl-7H-pyrrolo[2,3-d]pyrimidine (3, 19 g, 98.44 mmol) in dioxane (400 mL) and 2N sodium hydroxide solution (400 mL) was heated at 100° C. for 16 h. The reaction mixture was concentrated to remove dioxane. The aqueous residue was diluted with water (~200 mL) and acidified to pH ~4-6 using 1.5N hydrochloric acid solution. The precipitated solid was filtered, washed with hexane and dried under suction to afford the title compound 7-cyclopropyl-3,7-dihydro-4H-pyrrolo[2,3-d]pyrimidin-4-one (4, 14.93 g, 87% yield) as a brownish solid. Calculated (M+H): 176.07; Found (M+H): 176

Step-4: Preparation of ethyl 2-(7-cyclopropyl-4-oxo-4,7-dihydro-3H-pyrrolo[2,3-d]pyrimidin-3-yl)acetate (5)

To a solution of 7-cyclopropyl-3,7-dihydro-4H-pyrrolo[2,3-d]pyrimidin-4-one (4, 2.7 g, 15.41 mmol) in acetone (60 mL) were added ethyl 2-bromoacetate (5.1 g, 30.8 mmol) and potassium carbonate (6.2 g, 46.2 mmol) at room temperature and the reaction mixture was stirred at 55° C. for 4 h. The reaction mixture was cooled to room temperature and filtered. The solid was washed with ethyl acetate (100 mL) and the combined filtrate was evaporated to get crude product, which was purified by silica gel column chromatography using 40% ethyl acetate in hexane to afford the title compound ethyl 2-(7-cyclopropyl-4-oxo-4,7-dihydro-3H-pyrrolo[2,3-d]pyrimidin-3-yl)acetate (5, 3.5 g, 87% yield) as off-white solid. Calculated (M+H): 262.11; Found (M+H): 262

Step-5: Preparation of ethyl 2-(5-bromo-7-cyclopropyl-4-oxo-4,7-dihydro-3H-pyrrolo[2,3-d]pyrimidin-3-yl)acetate (6)

To a stirred solution of ethyl 2-(7-cyclopropyl-4-oxo-4,7-dihydro-3H-pyrrolo[2,3-d]pyrimidin-3-yl)acetate (5, 3 g, 11.4 mmol) in N,N-dimethyl formamide (200 mL), N,O-(bis-trimethylsilyl)acetamide (5.1 g, 25 mmol) and N-bromosuccinimide (2.02 g, 11.4 mmol) were added and the reaction mixture was stirred at room temperature for 2 h. The reaction mixture was quenched with cold water (400 mL) and extracted with ethyl acetate (2×200 mL). The combined organic layer was dried over anhydrous sodium sulphate, filtered and concentrated. The crude product was purified by silica gel column chromatography using 35% ethyl acetate in hexane to afford the title compound ethyl 2-(5-bromo-7-cyclopropyl-4-oxo-4,7-dihydro-3H-pyrrolo[2,3-d]pyrimidin-3-yl)acetate (6, 2.1 g, 54% yield) as an off white solid. Calculated (M+H): 340.02; Found (M+H): 340

Step-6: Preparation of 2-(5-(3-chloro-4-fluorophenyl)-7-cyclopropyl-4-oxo-4,7-dihydro-3H-pyrrolo[2,3-d]pyrimidin-3-yl)acetic acid (7)

To a solution of ethyl 2-(5-bromo-7-cyclopropyl-4-oxo-4,7-dihydro-3H-pyrrolo[2,3-d]pyrimidin-3-yl)acetate (6, 7.5 g, 22.04 mmol) and (3-chloro-4-fluorophenyl)boronic acid (5.76 g, 33.07 mmol) in 1,4-dioxane:water mixture (250 mL, 4:1), potassium carbonate (9.15 g, 66.14 mmol) was added. The reaction mixture was purged with argon for 20 min. Then [1,1'-bis(diphenylphosphino)ferrocene]dichloropalladium(II), complex with dichloromethane (0.9 g, 1.10 mmol) was added and the reaction mixture was stirred at 100° C. for 16 h. The reaction mixture was filtered through celite bed, the filtrate was diluted with water (100 mL) and washed with ethyl acetate (2×200 mL). The organic layer was discarded. The aqueous layer was acidified with 1.5N hydrochloric acid, the precipitated solid was filtered and dried under suction to afford the title compound 24543-chloro-4-fluorophenyl)-7-cyclopropyl-4-oxo-4,7-dihydro-3H-pyrrolo[2,3- d]pyrimidin-3-yl)acetic acid (7, 6 g, crude) as an off-white solid. Calculated (M+H): 362.06; Found (M+H): 362.1

Step-7: Preparation of 5-(3-chloro-4-fluorophenyl)-7-cyclopropyl-3-(2-(3-fluoro-3-methylazetidin-1-yl)-2-oxoethyl)-3,7-dihydro-4H-pyrrolo[2,3-d]pyrimidin-4-one To a stirred solution of 2-(5-(3-chloro-4-fluorophenyl)-7-cyclopropyl-4-oxo-4,7-dihydro-3H-pyrrolo[2,3-d]pyrimidin-3-yl)acetic acid (7, 1.8 g, 4.9 mmol) in dichloromethane (70 mL) were added triethylamine (1.36 mL, 9.9 mmol) and 3-fluoro-3-methylazetidine hydrochloride (1.24 g, 9.9 mmol) at room temperature. The reaction mixture was stirred for 10 min, then propylphosphonic anhydride solution (T$_3$P) (6.33 mL, 9.9 mmol, 50% in ethyl acetate) was added at 0° C. and reaction mixture was stirred at room temperature for 16 h. The reaction mixture was diluted with water (50 mL) and extracted with dichloromethane (3×70 mL). The combined organic layer was dried over anhydrous sodium sulfate, filtered and evaporated to get crude product, which was purified by silica gel column chromatography using 4% methanol in dichloromethane to afford the title compound 5-(3-chloro-4-fluorophenyl)-7-cyclopropyl-3-(2-(3-fluoro-3-methylazetidin-1-yl)-2-oxoethyl)-3,7-dihydro-4H-pyrrolo[2,3-d]pyrimidin-4-one (Compound 1, 1.1 g, 51% yield) as a white solid. Calculated (M+H): 433.12; Found (M+H): 433.1, $^1$H NMR (400 MHz, DMSO-d$_6$) δ (ppm): 8.26 (d, J=6 Hz, 1H), 8.15 (s, 1H), 7.93-7.91 (m, 1H), 7.58 (s, 1H), 7.35 (t, J=8.8 Hz, 1H), 4.67 (s, 2H), 4.45-4.32 (m, 2H), 4.05-3.97 (m, 2H), 3.64-3.59 (m, 1H). 1.61 (d, J=22 Hz, 3H), 1.10-1.00 (m, 4H). HPLC purity: 99.28%.

Example 2—Alternative Preparation of 5-(3-chloro-4-fluorophenyl)-7-cyclopropyl-3-(2-(3-fluoro-3-methylazetidin-1-yl)-2-oxoethyl)-3,7-dihydro-4H-pyrrolo[2,3-d]pyrimidin-4-one (Compound 1)

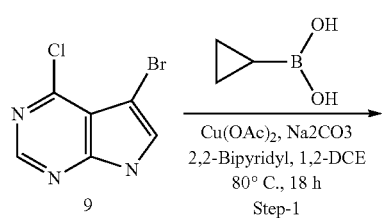

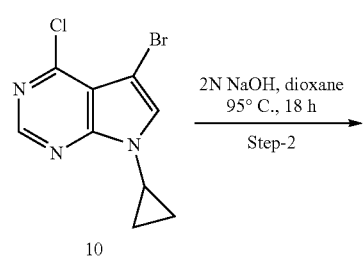

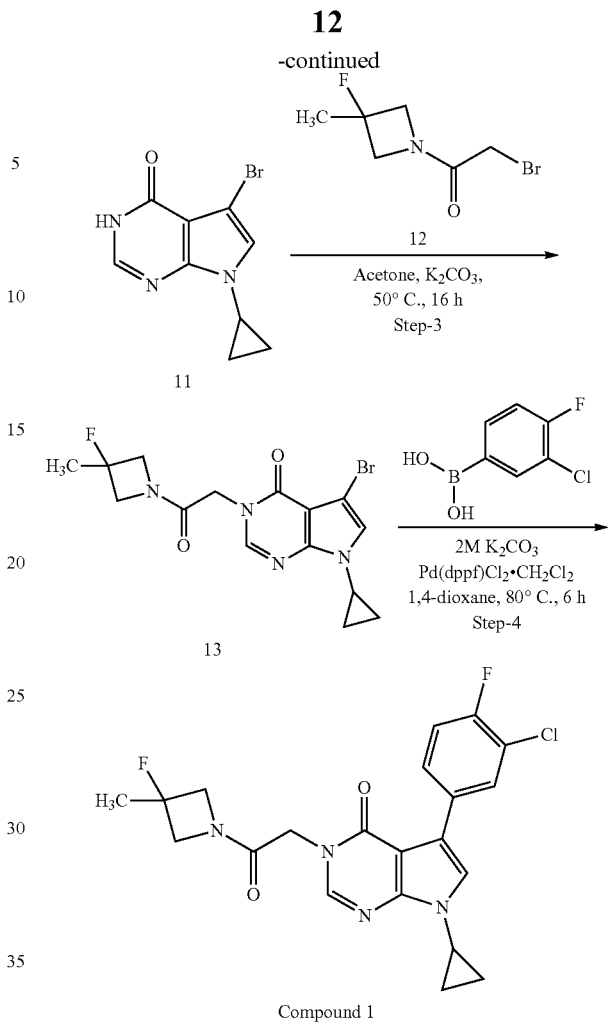

Compound 1

Step 1: Preparation of 5-bromo-4-chloro-7-cyclopropyl-7H-pyrrolo[2,3-d]pyrimidine 10

To a solution of 5-bromo-4-chloro-7H-pyrrolo[2,3-d]pyrimidine 9 (10.0 g, 43.10 mmol) in 1,2-dichloroethane (100.0 mL) were added cyclopropylboronic acid (7.41 g, 86.20 mmol), sodium carbonate (10.0 g, 86.20 mmol) and 2,2'-bipyridyl (6.70 g, 43.53 mmol). Then oxygen was purged into the reaction mixture for 30 min and copper acetate (8.21 g, 45.25 mmol) was added. The suspension was stirred at 80° C. for 18 h and after completion the reaction mixture was quenched with 1N hydrochloric acid at room temperature (up to pH=1.0). The solution was extracted with dichloromethane (4×100 mL) and the combined organic layer was dried over anhydrous sodium sulphate. The solution was concentrated and the residue was purified by silica gel column chromatography (using 10% ethyl acetate in hexane) to afford the title compound 5-bromo-4-chloro-7-cyclopropyl-7H-pyrrolo[2,3-d]pyrimidine 10 as off-white solid. Yield: 8.00 g, 68.4%. MS (ESI): m/z 271.94 [M+1]$^+$.

Step 2: Synthesis of 5-bromo-7-cyclopropyl-3,7-dihydro-4H-pyrrolo[2,3-d]pyrimidin-4-one (11)

A solution of 5-bromo-4-chloro-7-cyclopropyl-7H-pyrrolo[2,3-d]pyrimidine 10 (8.00 g, 29.52 mmol) in dioxane (40.00 mL) and 2N sodium hydroxide solution (40.00 mL)

was heated at 95° C. for 18 hours. After completion, the reaction mixture was concentrated to remove dioxane. The aqueous residue was diluted with water (about 50 mL) and acidified to pH of about 3 using 1N hydrochloric acid solution. The precipitated solid was filtered, washed with hexane and dried under suction to afford the title compound 5-bromo-7-cyclopropyl-3,7-dihydro-4H-pyrrolo[2,3-d]pyrimidin-4-one 11 as off white solid. Yield: 5.80 g, 77.70%. MS (ESI) m/z 254.05 [M+1]$^+$.

Synthesis of intermediate 2-bromo-1-(3-fluoro-3-methylazetidin-1-yl)ethan-1-one (12)

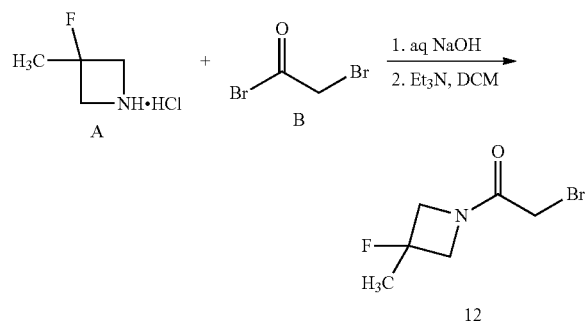

To a stirred solution of compound A (44.0 g, 352 mmol) in DCM (400 mL) was added NaOH (1.0 M solution, 14.0 g, 352 mmol) and stirred the biphasic solution at room temperature for 30 min. The solution was separated and the aqueous phase was extracted with DCM (50 mL). The combined organic layer was dried over anhydrous $Na_2SO_4$ and taken into a RBF. The solution was cooled to −10° C. and then bromoacetyl bromide B (106.5 mL, 528 mmol) was added slowly (to maintain the internal temperature at −5° C.) and stirred at same temperature for 2 h. After completion, the reaction mixture was quenched with cold sat $NaHCO_3$ solution and both layers were separated. The organic layer was dried over anhydrous $Na_2SO_4$ and concentrated under reduced pressure. The oily residue was quickly flashed through silica gel column (20-30% of EtOAc in hexanes) to afford 2-bromo-1-(3-fluoro-3-methylazetidin-1-yl)ethan-1-one 12 as light brown oil. Yield: 53.0 g (73%). MS (ESI) m/z 209.98 [M+1]$^+$.

Step 3: Synthesis of 5-bromo-7-cyclopropyl-3-(2-(3-fluoro-3-methylazetidin-1-yl)-2-oxoethyl)-3,7-dihydro-4H-pyrrolo[2,3-d]pyrimidin-4-one 13

To a solution of 5 bromo-7-cyclopropyl-3,7-dihydro-4H-pyrrolo[2,3-d]pyrimidin-4-one 11 (11.0 g, 43 mmol) in acetone (110 mL) were added 2-bromo-1-(3-fluoro-3-methylazetidin-1-yl)ethan-1-one 12 (10.9 g, 52 mmol) and $K_2CO_3$ (11.8 g, 86 mmol) at room temperature. The reaction mixture was stirred at 60° C. for 16 h. After completion, the reaction mixture was cooled to room temperature, filtered through Celite® and washed with acetone (500 mL). The combined filtrate was evaporated to get the crude product, which was purified by washing thoroughly with diethyl ether to afford the title compound 5-bromo-7-cyclopropyl-3-(2-(3-fluoro-3-methylazetidin-1-yl)-2-oxoethyl)-3,7-dihydro-4H-pyrrolo[2,3-d]pyrimidin-4-one 13 as a light brown solid. Yield: 14.9 g (89.7%). MS (ESI) m/z 294.23 [M+1]$^+$.

Step 4: Synthesis of 5-(3-chloro-4-fluorophenyl)-7-cyclopropyl-3-(2-(3-fluoro-3-methylazetidin-1-yl)-2-oxoethyl)-3,7-dihydro-4H-pyrrolo[2,3-d]pyrimidin-4-one (Compound 1)

To a solution of 5-bromo-7-cyclopropyl-3-(2-(3-fluoro-3-methylazetidin-1-yl)-2-oxoethyl)-3,7-dihydro-4H-pyrrolo[2,3-d]pyrimidin-4-one 13 (0.5 g, 1.3 mmol) in 1,4-dioxane (4.0 mL) were added (3-chloro-4-fluorophenyl)boronic acid (0.22 g, 1.3 mmol) and $K_2CO_3$ (0.36 g, 2.6 mmol, 2 M solution). The reaction mixture was first degassed with argon for 10 min and then $PdCl_2$(dppf) DCM (0.047 g, 0.065 mmol) was added under argon. The reaction mixture was stirred at 80° C. for 6 h. After completion, the reaction mixture was cooled to room temperature, filtered and washed with DCM (30 mL). The combined filtrate was evaporated to get the crude product, which was purified by silica gel column chromatography (5-6% methanol in DCM) and washed with THF to afford the title compound 5-(3-chloro-4-fluorophenyl)-7-cyclopropyl-3-(2-(3-fluoro-3-methylazetidin-1-yl)-2-oxoethyl)-3,7-dihydro-4H-pyrrolo[2,3-d]pyrimidin-4-one (Compound 1) as a light gray solid. Yield: 0.170 g (30%). MS (ESI) m/z 433.23 [M+1]$^+$.

Biological Assays

As shown by the data presented below, Compound 1 is a potent positive allosteric modulator across all of the NR2A, NR2B, NR2C and NR2D NMDA subtypes.

Oocyte 2EVC NR2A PAM Activity

In 2-electrode voltage clamp (2EVC) testing of oocytes expressing hNR2A and activated with 7 μM glutamate and 13 μM glycine, the potentiation of current (100% potentiation is equivalent to doubling of current induced by glutamate/glycine) and potency of Compound 1 was measured. $EC_{50}$ refers to the concentration of a compound that gives half-maximal response.

| Oocyte 2EVC NR2A PAM: Avg $EC_{50}$ (nM) | Oocyte 2EVC NR2A PAM: Avg Max % Potentiation (%) | Oocyte 2EVC NR2A PAM: Concentration Required for Current Doubling (nM) |
|---|---|---|
| 439 | 350 | 220 |

Oocyte 2EVC NR2C PAM Activity

Description: In 2-electrode voltage clamp (2EVC) testing of oocytes expressing hNR2C and activated with 10 μM glutamate and 10 μM glycine, the potentiation of current (100% potentiation is equivalent to doubling of current induced by glutamate/glycine) and potency of Compound 1 was measured. $EC_{50}$ refers to the concentration of a compound that gives half-maximal response.

| Oocyte 2EVC NR2C PAM: Average $EC_{50}$ (nM) | Oocyte 2EVC NR2C PAM: Avg Max % Potentiation (%) | Oocyte 2EVC NR2C PAM: Concentration Required for Current Doubling (nM) |
|---|---|---|
| 1203 | 1800 | 120 |

Oocyte 2EVC NR2D PAM Activity

Description: In 2-electrode voltage clamp (2EVC) testing of oocytes expressing hNR2D and activated with 10 μM glutamate and 10 μM glycine, the potentiation of current (100% potentiation is equivalent to doubling of current induced by glutamate/glycine) and potency of Compound 1 was measured. $EC_{50}$ refers to the concentration of a compound that gives half-maximal response.

| Oocyte 2EVC NR2D PAM: Average $EC_{50}$ (nM) | Oocyte 2EVC NR2D PAM: Avg Max % Potentiation (%) | Oocyte 2EVC NR2D PAM: Concentration Required for Current Doubling (nM) |
|---|---|---|
| 1887 | 1700 | 165 |

Oocyte 2EVC NR2B PAM Activity

In 2-electrode voltage clamp (2EVC) testing of oocytes expressing hNR2B and activated with 5 μM glutamate and 3 μM glycine, the potentiation of current (100% potentiation is equivalent to doubling of current induced by glutamate/glycine) and potency of Compound 1 was measured. $EC_{50}$ refers to the concentration of a compound that gives half-maximal response.

| Oocyte 2EVC NR2B PAM: Avg $EC_{50}$ (nM) | Oocyte 2EVC NR2B PAM: Avg Max % Potentiation (%) | Oocyte 2EVC NR2B PAM: Concentration Required for Current Doubling (nM) |
|---|---|---|
| 446 | 478 | 160 |

As shown in Table 1 below, Compound 1 was compared against Example 174 (the most potent exemplified compound tested in the Ro 25-6981/DCKA assay quantified by % response recovered) and Example 181 (the most potent exemplified compound tested in the Ro 25-6981/DCKA assay quantified by % maximum measured potentiation). As shown in the table, Compound 1 is approximately three-fold and 2.5-fold more potent in the oocyte NR2B PAM potentiation assay than Example 174 and Example 181, respectively. This improvement is advantageous because higher potency in the oocyte NR2B PAM potentiation assay is, in one aspect, anticipated to provide enhanced therapeutic benefit in humans

TABLE 1

| | Oocyte 2EVC NR2B PAM: $EC_{50}$ (nM) | Maximum measured potentiation (%) with Ro 25-6981 and DCKA | % response recovered with Ro 25-6981 and DCKA |
|---|---|---|---|
| 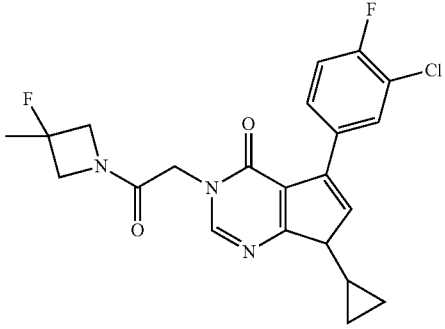<br>Compound 1 | 446 | Not determined | Not determined |

Comparator Examples from WO 2017/100591

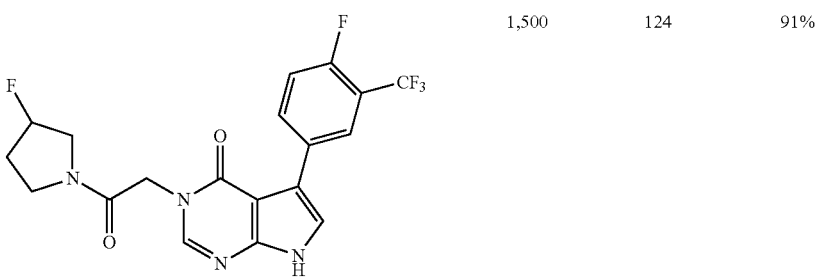

Example 174 — 1,500 — 124 — 91%

TABLE 1-continued

| | Oocyte 2EVC NR2B PAM: $EC_{50}$ (nM) | Maximum measured potentiation (%) with Ro 25-6981 and DCKA | % response recovered with Ro 25-6981 and DCKA |
|---|---|---|---|
| Example 181 | 1,190 | 129 | 69% |

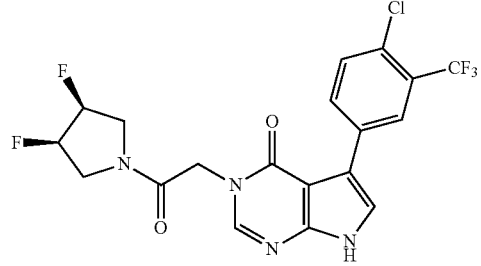

Solubility Determinations

The solubility of Compound 1 was investigated and compared with Example 436 of WO 2017/100591, a constitutional isomer (imidazopyrazinone core) of Compound 1 which demonstrated potency (100% response recovered) in the Ro 25-6981/DCKA assay. The aqueous solubility of the test compound was determined in phosphate buffer saline, pH 7.4, measured by shake-flask method. In this assay, DMSO stock solution of test compound was added to buffer followed by equilibration (shaking), filtration, and determination of soluble amount by HPLC-UV. As shown in the table, Compound 1 was found to have an approximate 10-fold increase in aqueous solubility (29 μM vs 3 μM) over the constitutional isomer Example 436. Other imidazopyrazinone comparators from WO 2017/100591 are provided for reference. All comparator analogs are active and potency data is available in WO 2017/100591. This improvement is advantageous because improved aqueous solubility, in one aspect, is anticipated to provide enhanced in vivo performance in humans.

TABLE 2

| | Aqueous solubility (uM) |
|---|---|
| Compound 1 | 29 |
| Key Comparator from WO 2017/100591 | |
| Example 436 | 3 |
| Additional Comparators from WO 2017/100591 | |
| Example 428 | 16 |

TABLE 2-continued
| | Aqueous solubility (uM) |
|---|---|
| 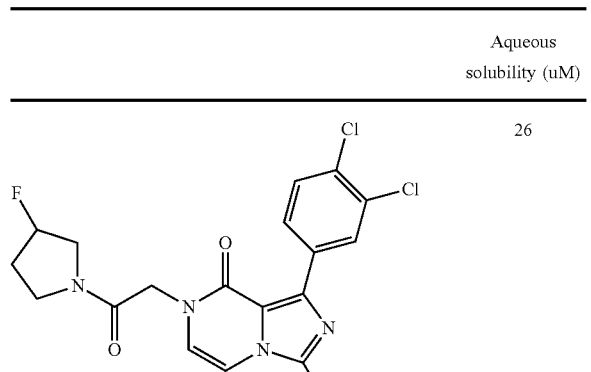<br>Example 429 | 26 |
| 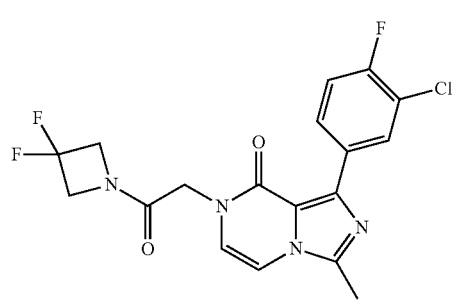<br>Example 430 | 43 |
| 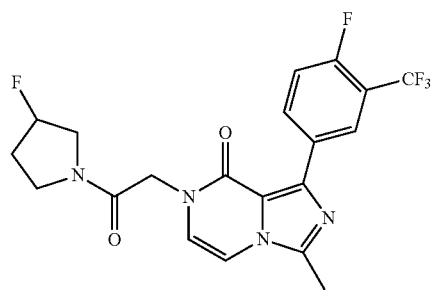<br>Example 427 | 7 |
| 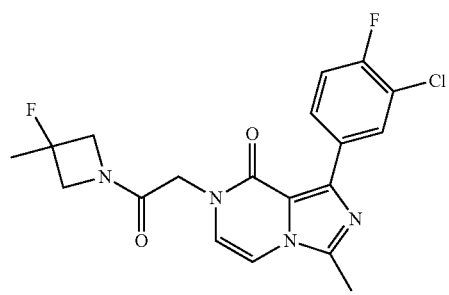<br>Example 426 | 20 |
TABLE 2-continued
| | Aqueous solubility (uM) |
|---|---|
| 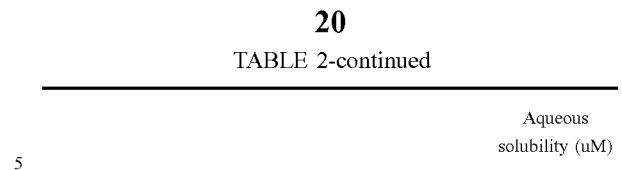<br>Example 432 | 4 |
| 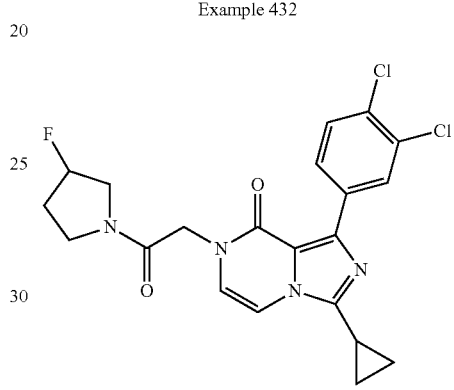<br>Example 433 | 30 |
| 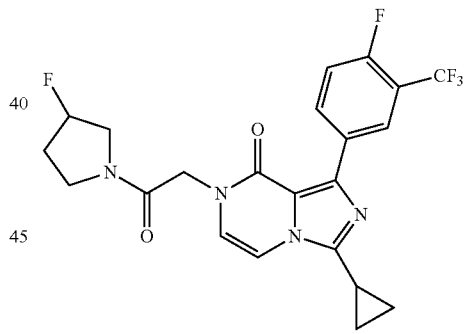<br>Example 434 | 5 |
| 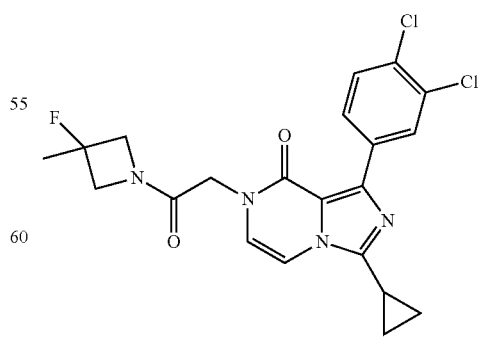<br>Example 435 | 14 |

TABLE 2-continued

| | Aqueous solubility (uM) |
|---|---|
| 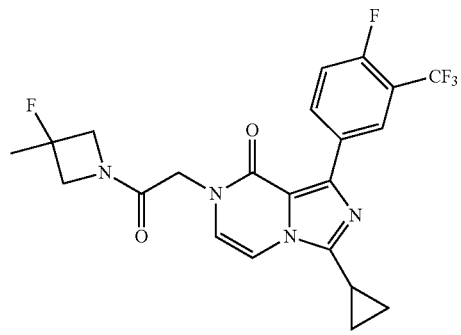 Example 438 | 2 |
| 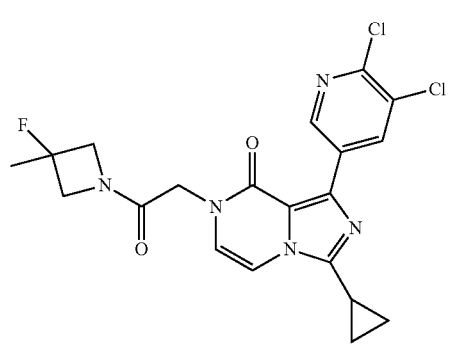 Example 437 | 7 |
| 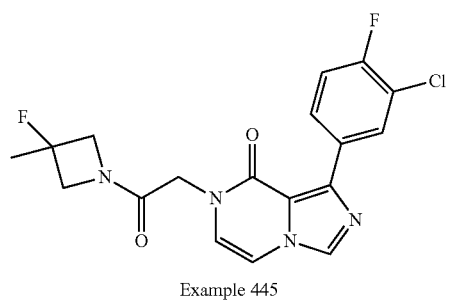 [SMILES: CC1(F)CN(C(=O)Cn2ccn3cnc(-c4ccc(F)c(Cl)c4)c3c2=O)C1] Example 445 | 14 |
| 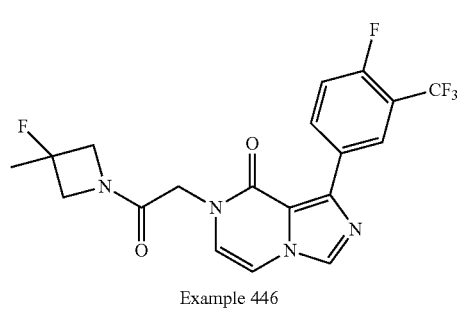 [SMILES: CC1(F)CN(C(=O)Cn2ccn3cnc(-c4ccc(F)c(C(F)(F)F)c4)c3c2=O)C1] Example 446 | 9 |

TABLE 2-continued

| | Aqueous solubility (uM) |
|---|---|
| 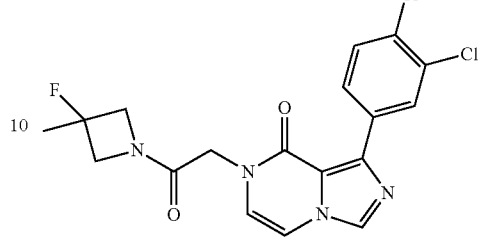 Example 447 | 69 |
| 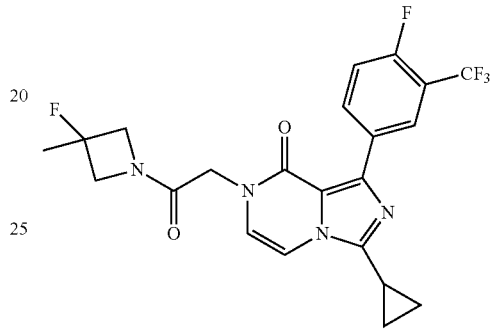 Example 438 | 2 |
| 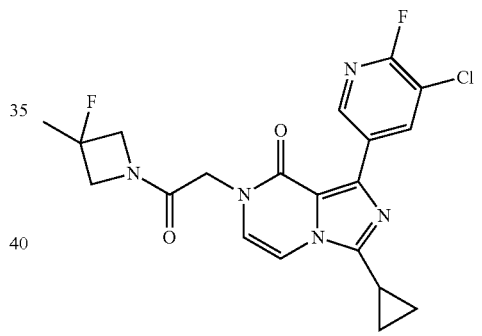 Example 441 | 3 |
| 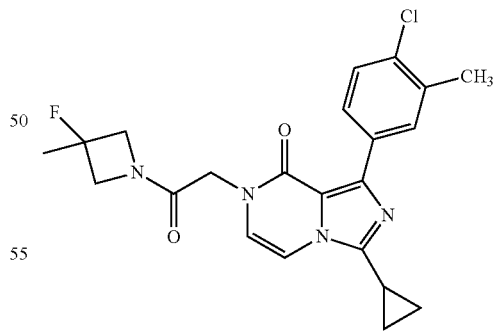 Example 443 | 91 |

Permeability and Efflux Determinations

Monolayer systems consist of a tight cell layer grown on a porous support to separate two fluid compartments. They are widely regarded as the most sophisticated in vitro tools for medium to high throughput modeling of important pharmacokinetic barriers, such as intestinal epithelium, blood-brain barrier, etc. (J Pharm Sci. 2012 April; 101(4): 1337-4354). Two systems that are applied widely in monolayer studies are the human colon carcinoma cell line Caco-2 and MDR1-transfected MDCKII and LLC-PK1 cells. In monolayer assays, the flux of a compound through the monolayer of cells is measured. The unidirectional flux of the compound of interest is determined by applying it to either the apical or to the basolateral side of the cell layer and monitoring the time resolved redistribution of it between the two compartments. The vectorial transport ratio (often referred to as Efflux Ratio) is determined by applying bidirectional measurements [apical-to-basolateral (A-B) and basolateral-to-apical (B-A)]. In general, a ratio higher than 2 or lower than 0.5 indicates the contribution of an active transport process to the net flux of a compound. In the absence of such transport processes this ratio is approximately 1.

TABLE 3

| A-B MDCK Permeability ($10^{-6}$ cm/sec) | B-A MDCK Permeability ($10^{-6}$ cm/sec) | Efflux Ratio |
| --- | --- | --- |
| 32.3 | 32.1 | 0.99 |

As shown in Table 3, Compound 1 penetrates membranes well and is not subject to efflux in the MDCK efflux assay.

Human and Rat Microsome Stability Determinations

The liver is the most important site of drug metabolism in the body. Approximately 60% of marketed compounds are cleared by hepatic CYP-mediated metabolism (McGinnity, D. F.; Soars, M. G.; Urbanowicz, R. A. and Riley, R. J.; Drug Metab. Disp. 32, 1247, (2004)). Liver microsomes are subcellular fractions which contain membrane bound drug metabolizing enzymes. Microsomes can be used to determine the in vitro intrinsic clearance of a compound. The use of species-specific microsomes can be used to enable an understanding of interspecies differences.

| HLM % Metabolized after 30 min | HLM $t_{1/2}$ (Min) | HLM $mCL_{int}$ (µL/min/mg) | RLM % Metabolized after 30 min | RLM $t_{1/2}$ (Min) | RLM $mCL_{int}$ (µL/min/mg) |
| --- | --- | --- | --- | --- | --- |
| 34.3 | 50.8 | 27.3 | 1.83 | >120 | <5 |

As shown, Compound 1 demonstrates good stability in Human Liver Microsomes (HLM) and excellent stability in Rat Liver Microsomes (RLM).

In Vivo Clearance

Compound 1 also exhibited improved in vitro microsomal stability and in vivo clearance in the rat IV pharmacokinetic study. As shown below, the in vivo clearance of Compound 1 is significantly lower than that of structurally-related NMDA PAMs exemplified in WO 2017/100591 for which IV rat clearance data is available. Of particular note is Example 285, a pyrrolopyridinone analog which demonstrated excellent potency in the Ro 25-6981/DCKA assay and is exceptionally structurally similar to Compound 1. Rat microsomal stability data is provided as well. These improvements in in vitro and in vivo clearance are advantageous because reduced clearance, in one aspect, is anticipated to provide enhanced in vivo performance in humans.

TABLE 4

| | Oocyte 2EVC NR2B PAM: $EC_{50}$ (nM) | Rat liver microsome (RLM) stability $t_{1/2}$ (min) | In vivo clearance (mL/min/kg) |
| --- | --- | --- | --- |
| | 446 | >120 | 7.4 |

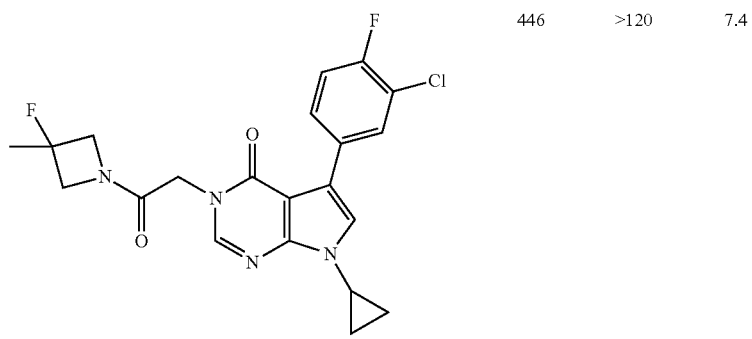

Compound 1

TABLE 4-continued
| | Oocyte 2EVC NR2B PAM: EC$_{50}$ (nM) | Rat liver microsome (RLM) stability t$_{1/2}$ (min) | In vivo clearance (mL/min/kg) |
|---|---|---|---|
| Key Comparator from WO 2017/100591 | | | |
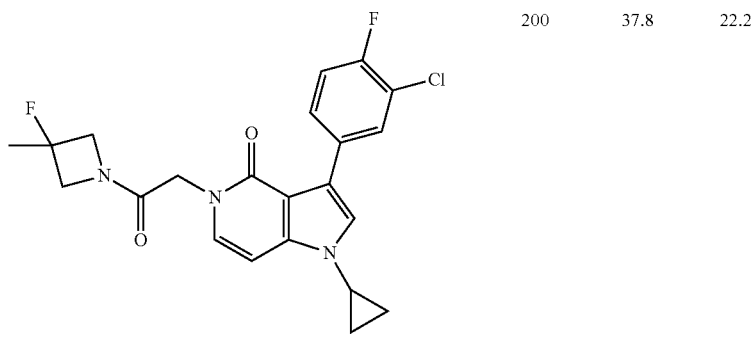
Example 285
| | 200 | 37.8 | 22.2 |
Additional Comparators from WO 2017/100591
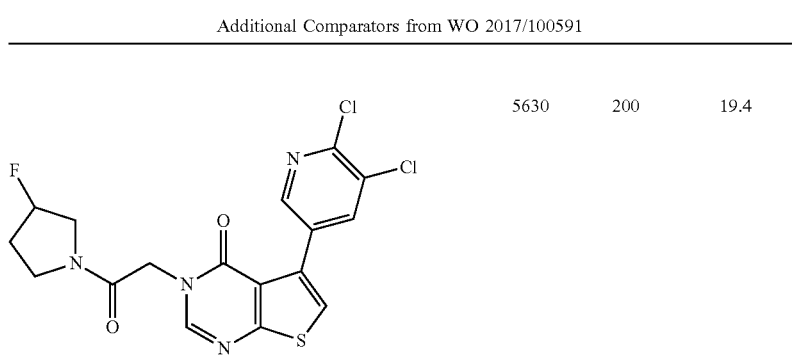
Example 12
| | 5630 | 200 | 19.4 |
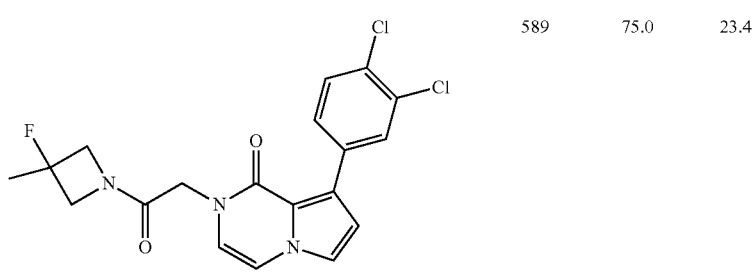
Example 396
| | 589 | 75.0 | 23.4 |
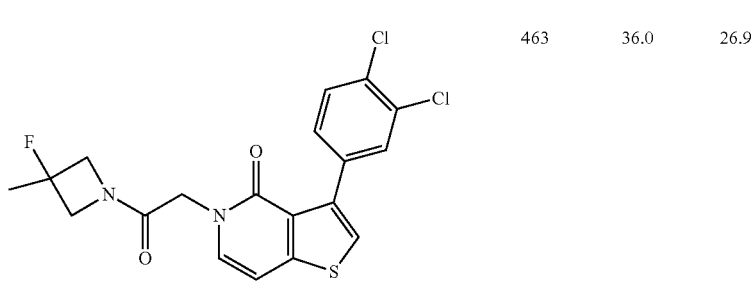
Example 42
| | 463 | 36.0 | 26.9 |

TABLE 4-continued
| | Oocyte 2EVC NR2B PAM: EC$_{50}$ (nM) | Rat liver microsome (RLM) stability t$_{1/2}$ (min) | In vivo clearance (mL/min/kg) |
|---|---|---|---|
| 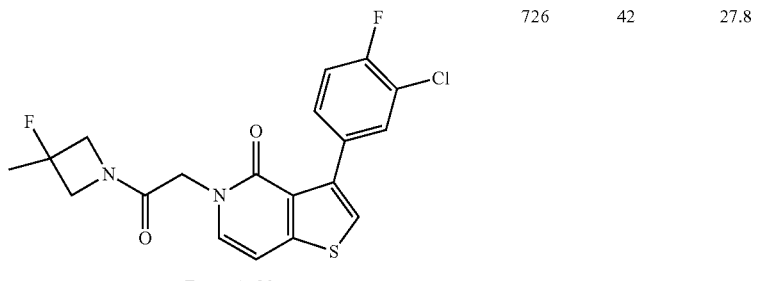 Example 39 | 726 | 42 | 27.8 |
| 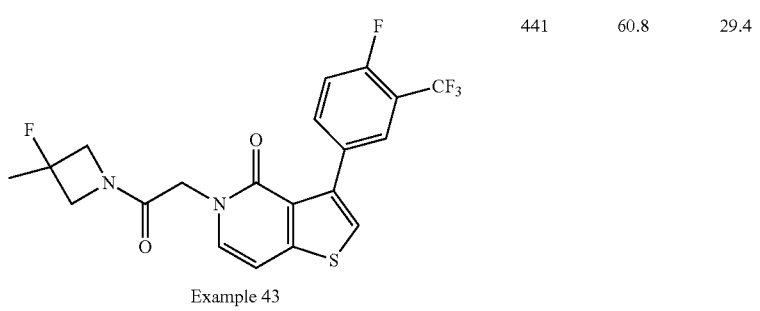 Example 43 | 441 | 60.8 | 29.4 |
| 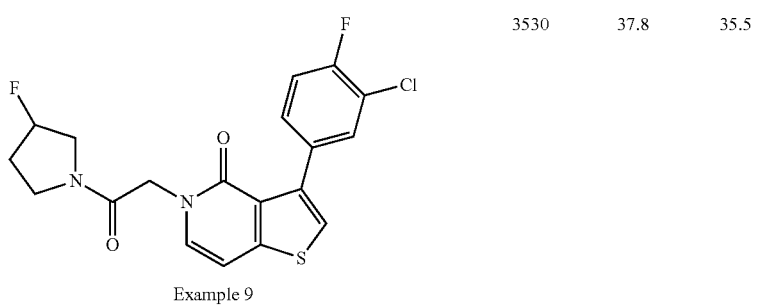 Example 9 | 3530 | 37.8 | 35.5 |
| 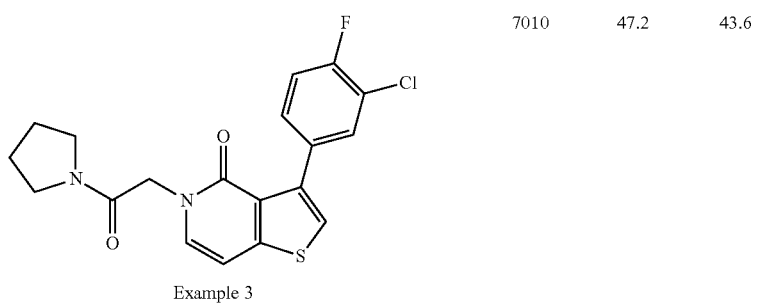 Example 3 | 7010 | 47.2 | 43.6 |

TABLE 4-continued

| | Oocyte 2EVC NR2B PAM: $EC_{50}$ (nM) | Rat liver microsome (RLM) stability $t_{1/2}$ (min) | In vivo clearance (mL/min/kg) |
|---|---|---|---|
| 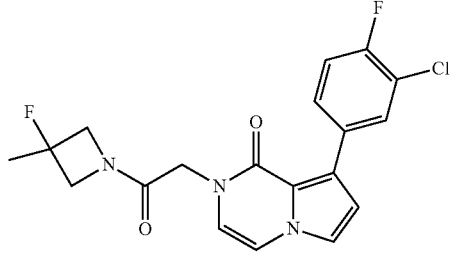<br>Example 397 | 1210 | 37.3 | 46.2 |

Pharmacology

A. Novel Object Recognition

The cognitive enhancing effect of oral Compound 1 (0.3, 1.0, and 3.0 mg/kg) was tested against phencyclidine (PCP)-induced cognitive impairment in the rat Novel Object Recognition (NOR) test. This experimental protocol tests for reversal of object recognition memory deficits caused by chronic administration of the NMDA receptor antagonist, PCP.

Rats were treated twice daily for 7 days with either saline vehicle (control group) or PCP (5 mg/kg, intraperitoneal). Following a 14-day washout period of no treatment, rats were tested in the NOR paradigm. Briefly, testing involves two sessions (T1 and T2), each lasting 3 minutes, 1 hour apart. Vehicle or Compound 1 were administered prior to the T1 trial. In T1, rats are placed in a test arena with two identical objects and allowed to freely explore while their time spent exploring each object is recorded. In T2, rats are returned to the test arena where one of the objects remains the same and the other has been replaced with a novel object. The time spent exploring the novel object versus the time spent exploring the familiar object are recorded and compared to T1 object exploration times.

Compared to saline control, PCP-treated animals showed a significant reduction in time spent exploring the novel object, confirming a PCP-induced deficit in NOR. As shown by the data in FIG. 1, administration of Compound 1 (0.3 and 1.0 mg/kg, oral) significantly reversed this deficit, as exhibited by an increased novel object exploration time compared to PCP-treated rats. The 1 mg/kg dose of Compound 1 fully-reversed the PCP-induced deficit, as the exploration time at these doses was not significantly different from that in saline control animals.

B. Mismatch Negativity Efficacy Model

Pathophysiological biomarkers of NMDA receptor hypofunction in schizophrenia include EEG measurements of early auditory processing events, such as "Mismatch Negativity", an EEG Event-Related Potential (ERP) that measures pre-attentional auditory novelty detection. MMN is a translatable measure of auditory novelty detection in rats and humans, and is correlated with cognitive and global function in patients with schizophrenia. NMDA receptor antagonists PCP, MK-801, and ketamine elicit acute deficits in MMN in rats (all three NMDAr antagonists) and human subjects (ketamine)

Rats implanted with frontal EEG electrodes were presented with different audio stimuli comprising an auditory oddball "flip-flop" protocol. Briefly, 1,000 standard tones of 6.0 kHz were delivered at 90% probability, and 100 deviant tones of 8.0 kHz were delivered at 10% probability in pseudo-random order (the flip sequence), and then this sequence was then repeated with the 8 kHz tone as the standard, and the 6 kHz tone as the deviant (the flop sequence). MMN is calculated as a difference potential obtained by subtracting the averaged 8 kHz standard tone response (flop) from the averaged 8 kHz deviance tone response (flip) at each 1 ms time point over the EEG recording epochs from 50 ms prior to 150 ms after the onset of these 50 ms auditory tones.

Figure 2:
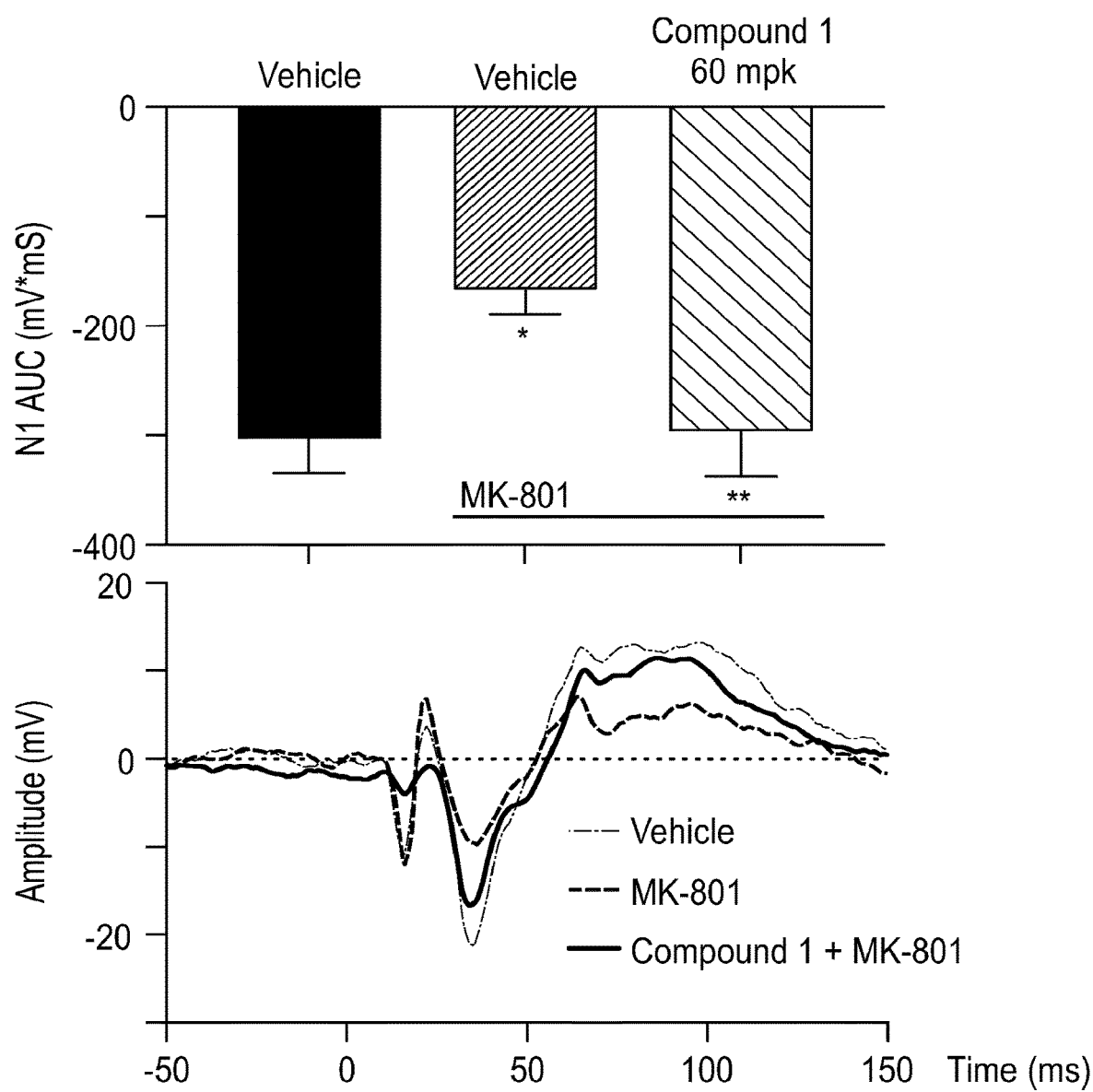
FIG. 2 illustrates the results from Compound 1 in a mismatch negativity efficacy model.

In a 4-way crossover design, rats were dosed with vehicle or Compound 1 (60 mg/kg) twice, 4 hours apart. Rats were then dosed with saline control or MK-801 (0.2 mg/kg, IP) immediately prior to test sessions. Test sessions were comprised of three 20-minute flip-flop blocks. As shown by FIG. 2, administration of vehicle plus MK-801 significantly impaired MMN compared to administration of vehicle plus saline. In addition, administration of Compound 1 (60 mg/kg BID) prevented impairment of MMN by MK-801, such that MMN recorded after Compound 1 plus MK-801 was no longer different from MMN recorded after vehicle and saline, and was significantly larger when compared to MMN recorded after administration of vehicle and MK-801.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

The invention claimed is:

1. A method for treating cognitive impairments resulting from neurological diseases selected from dementia, Alzheimer's disease, Parkinson's disease, Huntington's disease, amyotrophic lateral sclerosis, multiple sclerosis, and seizure disorders in a subject in need thereof, comprising administering to said subject a therapeutically effective amount of a compound of the formula:

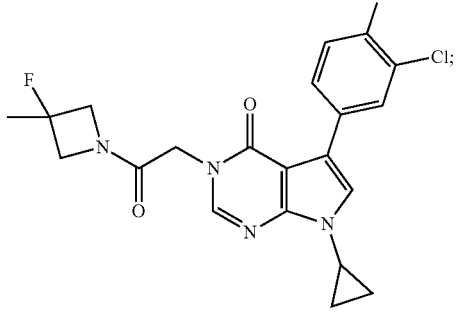

or a pharmaceutically acceptable salt thereof.

2. A method of treating cognitive impairment associated with schizophrenia comprising administering to a subject in need thereof a therapeutically effective amount of a compound of the formula

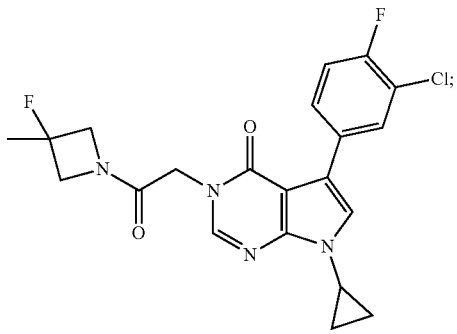 [SMILES: CC1(F)CN(C(=O)Cn2cnc3c(c(-c4ccc(F)c(Cl)c4)cn3C3CC3)c2=O)C1]

or a pharmaceutically acceptable salt thereof.

3. A method of treating Phelan-McDermid Syndrome comprising administering to a subject in need thereof a therapeutically effective amount of a compound of the formula

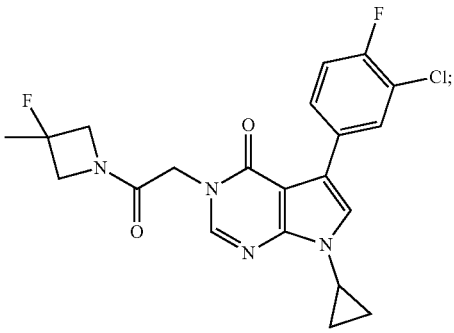 [SMILES: CC1(F)CN(C(=O)Cn2cnc3c(c(-c4ccc(F)c(Cl)c4)cn3C3CC3)c2=O)C1]

or a pharmaceutically acceptable salt thereof.

4. A method of positively allosterically modulating NMDA ion channel receptors in a subject in need thereof comprising administering to the subject a therapeutically effective amount of a compound of the formula

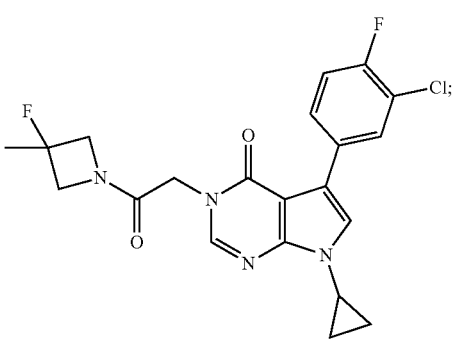 [SMILES: CC1(F)CN(C(=O)Cn2cnc3c(c(-c4ccc(F)c(Cl)c4)cn3C3CC3)c2=O)C1]

or a pharmaceutically acceptable salt thereof.

5. The method of claim 4, wherein the diseases treatable by said modulation are selected from neuropsychiatric, neurodevelopmental, and neurological disorders.

* * * * *